US00PP09459P

United States Patent [19]

Mak

[11] Patent Number: Plant 9,459

[45] Date of Patent: Feb. 27, 1996

[54] LILY PLANT NAMED 'SIBERIA'

[75] Inventor: Johannes A. Mak, Independence, Oreg.

[73] Assignee: Siberia Oriental B.V., Netherlands

[21] Appl. No.: 396,651

[22] Filed: Feb. 9, 1995

[51] Int. Cl.[6] ..... A01H 5/00

[52] U.S. Cl. ..... Plt./87.4

[58] Field of Search ..... Plt./87.4

*Primary Examiner*—James R. Feyrer

*Attorney, Agent, or Firm*—Greer, Burns & Crain, Ltd.

[57] ABSTRACT

A new and distinct clonal lily cultivar of the Oriental hybrid type, having a large stature and good growth, bright green leaves, long lasting outwardly facing large bowl-shaped flowers of white coloration and good disease resistance.

1 Drawing Sheet

BACKGROUND OF THE NEW PLANT

My new variety of lily plant herein disclosed originated as a seedling of unknown parentage discovered by me at my nursery in The Netherlands, in May 1987.

This particular seedling was selected for propagation because of its large size, its white, erect and long-lasting flowers, its strong growth and good virus resistance. This selected seedling was asexually reproduced by me and under my direction at my nursery in The Netherlands 't Zand, and successive generations produced by bulb scale propagation, natural propagation from bulbets and tissue culture in laboratories which have demonstrated that this new lily plant has the desirable characteristics of hybrid vigor, great hardiness, and a high degree of disease resistance, as well as all of the desirable characteristics of form, color and habit. This generation to generation propagation has also shown that the plant is a vigorous and good grower and propagator, and that its clones force well for cut-flower production as observed at my nursery in The Netherlands, 't Zand, and that the novel and distinctive characteristics of this new variety hold true under asexual proparation from generation to generation and appear to be firmly fixed.

DESCRIPTION OF THE DRAWING

This new variety of lily plant is illustrated in the accompanying photographic drawing, which shows the upper half portion of the flowering stem of a potted plant in the upper view and full face view of the flower of this plant together with foliage and buds, the color rendition being as nearly true as can be reasonably obtained by conventional photographic procedures.

DESCRIPTION OF THE NEW VARIETY

The following is a detailed description of my new Oriental hybrid lily cultivar according to observations made on greenhouse and filed grown plants in 't Zand and Wageningen in The Netherlands with color designations according to The R.H.S. Colour Chart published by The Royal Horticultural Society of London, England, and with nomenclature according to The International Lily Register, also published by The Royal Horiticultural Society.

THE PLANT

Origin: Seedling.
Parentage: Unknown.
Classification:
- *Botanic.*—Hybrid lily cultivar.
- *Commercial.*—Oriental hybrid lily.

Form: Single stem from each bulb, erect and bushy.
Height: About 90–110 cm.
Growth: Vigorous and upright with good strength.
Foliage:
- *Quantity.*—Abundant
- *Size of leaf.*—About 16 cm. long and about6 cm. wide at the base.
- *Shape of leaf.*—Broad lanceolate.
- *Margin.*—Entire.
- *Aspect.*—Glossy.
- *Texture.*—Smooth.
- *Color.*—Upper Side: Bright Green (R.H.S. 137–A). Under Side: Light Green (R.H.S. 137–C).

Bulbs:
- *Size.*—Vary with age. At year one, the size of the bulb ranges from 4–7 cm. in circumference. At year two, the size of the bulb ranges from 12–16 cm. in circumference. From year three and on, the size of the bulb is at least 16 cm. in circumference.
- *Color.*—The color os the bulbs is typical of Oriental hybrid bulbs. The bulbs are white on the under side and yellow on the top. Before fading to yellow, the white becomes speckled with yellow spots.

THE BUD

Form: Generally long with pointed ends.
Size: About 14 cm. in length and about 13 cm. in circumference.
Opening rate: The bud opens slowly, in about 1–2 days at 18°–21° C. The buds open successively from lowermost to uppermost, typical of Lilium
Color: The color of the bud is a soft green, no semicolor, R.H.S. 144-B, which turns to white, R.H.S. 155-D, prior to the tepals unfurlong.
Peduncle; Is about 5–6 cm. long and green (R.H.S. 144-B) in color.

THE FLOWER

Blooming habit: Intermittent and profusely. When planted in a field in April, Siberia flowers in August. Siberia will bloom in approximately 110 days from planting in a greenhouse.
Size of flower: Large, approximately 27 cm. in diameter and 8 cm. deep.
Borne: As a compact raceme with each pedicel bearing one bud. Bulbs of typical commercial size bear an average of 6 to 8 flowers.
Shape: Bowl-Shaped with broad and overlapping tepals, where the ends of the tepals are recurved.

Tepalage:
*Number.*—Six.
*Shape.*—Generally ovoid with undulated margins.
*Arrangement.*—Imbricated.
*Color.*—White (R.H.S. 155-D).

Color change: The color fades slightly and becomes more brown as the flower ages or is exposed to intense light and heat. The color lasts longer and is richer under cooler conditions.

Tepal longevity: Tepals stay on the stem for approximately three weeks.

Pedicel:
*Length.*—About 5–6 cm.
*Color.*—Green (R.H.S. 144-B).

Fragrance: The fragrance is sweet and light.

Disease resistance: The flower and plant are resistant to disease. In particular, the flower and plant are resistant to Botrytis and *Fusarium oxysporum.*

Lasting quality: As a cut flower, the flower lasts approximately 2 to 3 weeks. On the plant, the flowers last approximately 4 weeks.

THE REPRODUCTIVE ORGANS

Stamens:
*Number.*—Six.
*Arrangement.*—Around the pistil.

Anthers:
*Size.*—Approximately 4 cm.
*Color.*—Orange (R.H.S. 28-B).

Filaments: Approximately 6–7 cm. long and green to white in color.

Style: Approximately 8–9 cm. long and green in color.

Stigma: Purple-red in color.

Ovary: Typical of genus Lilium.

THE FRUIT

Fertility: The fruit is fertile.

Shape: Pear-shaped.

Color: Greenish-brown.

The cumulative features of this new lily plant indicate that this cultivar has definite advantages of commercial value and that in general this new plant provides a valuable addition to the commercial production of potted lilies.

I claim:

1. A new and distinctive variety of Orintal hybrid lily, substantially as herein shown and described, characterized by its large stature and good growth, its large leaves of bright green color, its outwardly facing, bowl-shaped flowers of large size and white coloration, and its good disease resistance.

* * * * *

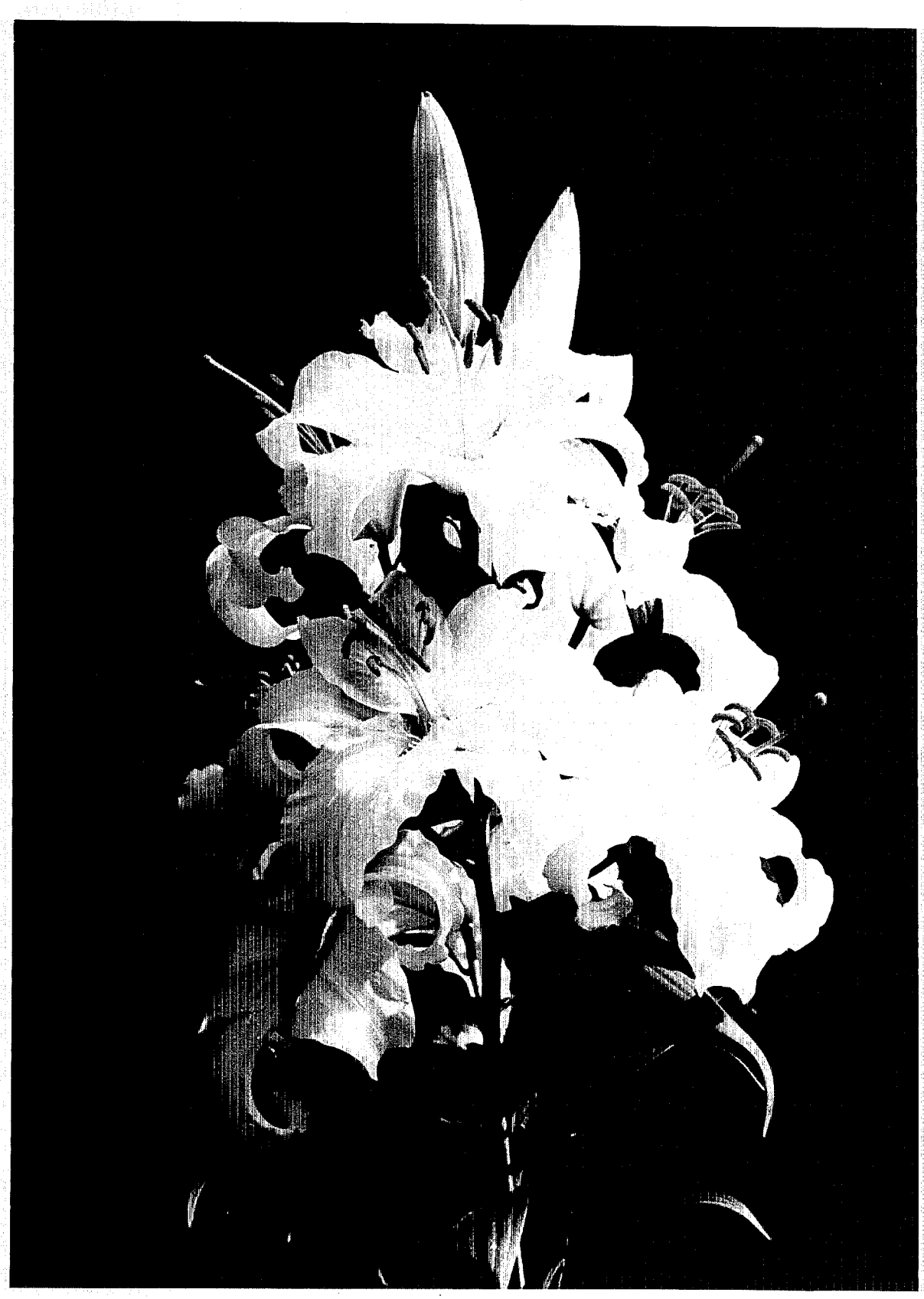

UNITED STATES PATENT AND TRADEMARK OFFICE

CERTIFICATE OF CORRECTION

PATENT NO. : PP 9,459
DATED : February 27, 1996
INVENTOR(S) : Johannes A. Mak

It is certified that error appears in the above-indentified patent and that said Letters Patent is hereby corrected as shown below:

On page 1, column 2, line 6, under the "Size of leaf", a space is missing between "about" and "6".

On page 1, column 2, line 20, under "color", delete "os" and insert --of--.

On page 1, column 2, line 34, delete "unfurlong" and insert --unfurling--.

On page 2, column 4, line 20, delete "Orintal" and insert --Oriental--.

Signed and Sealed this

Fifteenth Day of October, 1996

*Attest:*

*Attesting Officer*

BRUCE LEHMAN

*Commissioner of Patents and Trademarks*